United States Patent [19]
Schraer et al.

[11] Patent Number: 6,139,826
[45] Date of Patent: *Oct. 31, 2000

[54] PERSONAL CARE COMPOSITIONS CONTAINING A COPOLYMER HAVING HYDROPHOBIC, CARBON-BASED GRAFTS

[75] Inventors: Robert Michael Schraer, Fairfield; Peter Marte Torgerson, Court House; Sanjeev Midha, Blue Ash, all of Ohio

[73] Assignee: The Procter & Gamble Company, Cincinnati, Ohio

[ * ] Notice: This patent is subject to a terminal disclaimer.

[21] Appl. No.: 08/616,401

[22] Filed: Mar. 15, 1996

[51] Int. Cl.$^7$ .............................. A61K 7/11; A61K 47/32
[52] U.S. Cl. ...................... 424/70.16; 424/70.17; 424/78.18; 424/DIG. 1; 424/DIG. 2; 424/47
[58] Field of Search .................. 424/401, 70.16, 424/70.17, 78.18, DIG. 2, DIG. 1; 525/70, 326.1, 329.7, 330.3

[56] References Cited

U.S. PATENT DOCUMENTS

| | | | |
|---|---|---|---|
| 3,697,643 | 10/1972 | Shepherd et al. | 424/63 |
| 3,786,116 | 1/1974 | Milkovich et al. . | |
| 3,907,984 | 9/1975 | Calvert et al. | 424/47 |
| 4,059,688 | 11/1977 | Rosenberg et al. | 424/71 |
| 4,722,958 | 2/1988 | Sauer et al. | 524/379 |
| 4,798,721 | 1/1989 | Yahagi et al. | 424/70 |
| 4,963,348 | 10/1990 | Bolich, Jr. et al. | 424/71 |
| 4,981,902 | 1/1991 | Mitra et al. | 524/547 |
| 4,981,903 | 1/1991 | Garbe et al. | 524/547 |
| 4,985,239 | 1/1991 | Yahagi et al. | 424/70 |
| 4,988,506 | 1/1991 | Mitra et al. | 424/81 |
| 5,009,880 | 4/1991 | Grollier et al. | 424/47 |
| 5,019,377 | 5/1991 | Torgerson | 424/70 |
| 5,021,477 | 6/1991 | Garbe et al. | 424/70 |
| 5,073,371 | 12/1991 | Turner et al. | 424/401 |
| 5,073,372 | 12/1991 | Turner et al. | 424/401 |
| 5,104,642 | 4/1992 | Wells et al. | 424/47 |
| 5,106,609 | 4/1992 | Bolich, Jr. et al. . | |
| 5,120,531 | 6/1992 | Wells et al. | 424/70 |
| 5,120,532 | 6/1992 | Wells et al. | 424/70 |
| 5,166,276 | 11/1992 | Hayama et al. | 525/329 |
| 5,179,158 | 1/1993 | Azuma et al. . | |
| 5,219,560 | 6/1993 | Suzuki et al. | 424/63 |
| 5,223,179 | 6/1993 | Connor et al. | 252/548 |
| 5,256,407 | 10/1993 | Gough | 424/71 |
| 5,286,755 | 2/1994 | Kauffmann et al. | 514/944 |
| 5,290,555 | 3/1994 | Guthauser et al. | 424/401 |
| 5,324,507 | 6/1994 | Dubief et al. | 424/70 |
| 5,342,883 | 8/1994 | Jenkins et al. . | |
| 5,356,627 | 10/1994 | Da Cunha et al. | 424/401 |
| 5,362,485 | 11/1994 | Hayama et al. | 424/70 |
| 5,372,804 | 12/1994 | Khoshdel et al. | 424/59 |
| 5,374,421 | 12/1994 | Tashiro et al. | 424/70.12 |
| 5,391,368 | 2/1995 | Gerstein | 424/70.13 |
| 5,632,998 | 5/1997 | Midha et al. . | |

FOREIGN PATENT DOCUMENTS

| | | | |
|---|---|---|---|
| 647849 | 6/1992 | Australia | A61K 0/07 |
| 0 412704 A2 | 2/1991 | European Pat. Off. | A61K 7/06 |
| 4314305 A1 | 3/1994 | Germany | A61K 7/11 |
| 2-25411 | 1/1990 | Japan . | |
| 2 144 133 | 2/1985 | United Kingdom | C08L 33/00 |
| 92/16187 | 10/1992 | WIPO | A61K 7/06 |
| WO 92/21319 | 12/1992 | WIPO | A61K 7/06 |
| WO 95/04518 | 2/1995 | WIPO | A61K 7/06 |
| WO 95/05800 | 3/1995 | WIPO | A61K 7/48 |
| 96/00562 | 1/1996 | WIPO | A61K 7/06 |
| 96/20691 | 7/1996 | WIPO | A61K 7/11 |
| WO 97/35541 | 2/1997 | WIPO | A61K 7/06 |

*Primary Examiner*—Edward J. Webman
*Attorney, Agent, or Firm*—Tara M. Rosnell; Andrew A Paul

[57] ABSTRACT

Disclosed are personal care compositions, especially hair styling compositions containing:

(a) a graft copolymer characterized by having a hydrophilic organic polymeric backbone and hydrophobic macromonomers grafted to said backbone; the hydrophilic polymeric backbone having a Tg of at least about −20° C.; the hydrophobic macromonomers having a carbon based main chain; a Tg of less than about 0° C. and a number average molecular weight of at least about 500; and (b) a hydrophilic solvent preferably selected from the group consisting of water, $C_2$–$C_3$ monohydric alcohols and mixtures thereof.

24 Claims, No Drawings

6,139,826

1

PERSONAL CARE COMPOSITIONS CONTAINING A COPOLYMER HAVING HYDROPHOBIC, CARBON-BASED GRAFTS

TECHNICAL FIELD

The present invention relates to personal care compositions, especially hair styling compositions, containing a graft copolymer as a hair setting agent. More particularly, the present invention relates to hair styling compositions containing a graft copolymer and a hydrophilic solvent. The graft copolymer has an organic, hydrophilic backbone and grafts comprising a hydrophobic macromonomer chemically joined and pendant thereto.

BACKGROUND OF THE INVENTION

The desire to have the hair retain a particular shape is widely held. The most common methodology for accomplishing this is the application of a composition to dampened hair, after shampooing and/or conditioning, or to dry, styled hair. These compositions provide temporary setting benefits and they can be removed by water or by shampooing. The materials used in the compositions to provide the setting benefits have generally been resins and have been applied in the form of mousses, gels, lotions or sprays.

Many people desire a high level of style retention, or hold, from a hair spray composition. In typical hair sprays, hold is achieved by the use of resins such as AMPHOMER$^R$, supplied by National Starch and Chemical Company, and GANTREZ$^R$, supplied by GAF. In general, as hair hold for hair spray compositions is increased, the tactile feel of the hair becomes stiffer and hence, less desirable. It is desirable to provide hair spray products which could provide an improved combination of hair hold and hair feel characteristics.

One known approach to improving hair feel has been the use of plasticizers in the hair styling composition. Unfortunately, plasticizers tend to increase the tackiness of the hair styling product when in use, and to cause a decrease in the level of hair hold.

It is also known to utilize silicone grafted organic backbone polymers as hair setting agents in hairspray compositions and other hair styling compositions, e.g. hair tonics, lotions, rinses, mousses, etc. Silicone graft copolymers can be used to make hair spray compositions which provide hair setting ability with improved hair feel, e.g., increased softness relative to conventional polymeric hair setting agents. Unfortunately, the improvements in hair feel are often at the sacrifice of some level of hair hold ability.

Thus, while hair styling compositions known heretofore provide certain hair feel benefits, it remains desirable to provide hair styling compositions which have improved hair hold (after application and drying of such compositions) for a particular level of hair feel performance or, conversely, an improved hair feel performance at a particular level of hair hold. It is a particular challenge to improve hair hold while retaining or improving upon the hair feel typically provided by silicone graft copolymers.

Hair sprays have been conventionally formulated with high amounts of monohydric alcohol solvents, such as ethanol and isopropanol, and relatively low amounts of water since the presence of water adversely affects spray quality. However, it is now particularly desirable to formulate hair spray compositions with reduced levels of volatile organic compounds, such as ethanol, isopropanol, and other volatile materials, such as aerosol propellants. One way to do this is to increase the levels of water in the formulations. In doing so, it would be highly desirable to provide reformulated products which overcome the problems conventionally associated with the addition of water to hair spray products. In particular, higher levels of water can negatively impact hair feel.

It is an object of this invention to provide hair styling compositions, and especially hair spray compositions and other aqueous, alcoholic, or hydroalcoholic-based hair setting solutions, containing hair setting agents that provide improved combinations of hair feel/hair hold performance.

It is a further object of this invention to provide hair styling compositions, as described above, that provide both improved hair feel and improved hair hold ability for a particular level of hair setting agent in the composition.

It is yet a further object of this invention to provide compositions that meet the above objects for conventional volatile organic compound level ("conventional VOC") compositions, which typically contain greater than 80% of volatile organic compounds, as well as for reduced volatile organic compound level ("reduced VOC") compositions, i.e., compositions having 80% or less volatile organic compounds.

These and other benefits as may be apparent from the description below can be obtained by the present invention.

SUMMARY OF THE INVENTION

The present invention relates to personal care compositions, preferably hair care compositions, comprising:

(a) from about 0.1% to about 15%, by weight, of a graft copolymer, said polymer being characterized by a hydrophilic organic polymeric backbone having hydrophobic macromonomers grafted to said backbone; said hydrophilic polymeric backbone having a $T_g$ of at least about −20° C.; said hydrophobic macromonomers characterized by having a carbon based main chain; said hydrophobic macromonomers having a $T_g$ of less than about 0° C. and a number average molecular weight of at least about 500; and (b) from about 99.9% to about 85%, by weight, of a carrier for said graft copolymer, said carrier comprising a hydrophilic solvent, preferably selected from the group consisting of water, $C_2$–$C_3$ monohydric alcohols and mixtures thereof, wherein said graft copolymer is substantially soluble in said solvent.

In a preferred embodiment, the composition comprises from about 20% to about 99.9%, by weight of the composition, of the hydrophilic solvent and more preferably no more than about 15%, by weight, of $C_3$ monohydric alcohol.

In preferred embodiments, the compositions hereof additionally comprise a plasticizer for the graft copolymer. Also in preferred embodiments, the compositions hereof additionally comprise from about 0.1% to about 15%, by weight, of a volatile hydrocarbon solvent selected from the group consisting of $C_{10}$–$C_{16}$ branched chain hydrocarbons, and mixtures thereof, the hydrocarbon solvent preferably having a boiling point of from about 105° C. to about 260° C.

The hydrophilic polymeric backbone has a relatively high strength. Without intending to be bound by theory, it is believed that the hydrophobic macromonomers that are grafted to the backbone reduce the brittleness of the backbone, improving the elongation to break without unacceptably diminishing strength.

DETAILED DESCRIPTION OF THE INVENTION

The essential components of the present invention are described below. Also included is a nonexclusive description of various optional and preferred components useful in embodiments of the present invention.

The present compositions can comprise, consist of, or consist essentially of any of the required or optional ingredients and/or limitations described herein.

All percentages and ratios are calculated on a weight basis unless otherwise indicated. All percentages are calculated based upon the total composition unless otherwise indicated.

All ingredient levels are in reference to the active level of that ingredient, and are exclusive of solvents, by-products, or other impurities that may be present in commercially available sources, unless otherwise indicated.

All documents referred to herein, including all patents, patent applications, and printed publications, are hereby incorporated by reference in their entirety in this disclosure.

Graft Adhesive Polymer

The compositions of the present invention essentially comprise a graft adhesive copolymer as a hair setting agent (alternatively referred to herein as "graft copolymer"). The compositions hereof will generally comprise from about 0.1% to about 15%, preferably from 0.5% to about 8%, more preferably from about 1% to about 8%, by weight of the composition, of the graft copolymer. It is not intended to exclude the use of higher or lower levels of the graft copolymers, as long as an effective amount is used to provide adhesive or film-forming properties to the composition and the composition can be formulated and effectively applied for its intended purpose. By "adhesive copolymer" it is meant that when applied as a solution to a surface and dried, the copolymer forms a film. Such a film will have adhesive and cohesive strength, as is understood by those skilled in the art.

The graft copolymer is characterized by a hydrophilic, polymeric backbone with a hydrophobic macromonomer covalently bonded to and pendant from the polymer backbone (the hydrophobic macromonomer(s) are grafted to the polymer backbone). As will be clear to one skilled in the art and especially from the synthetic examples, the graft copolymer may have one or more hydrophobic macromonomers grafted to the backbone. In addition, the compositions of the present invention may include, in addition to the graft copolymer, corresponding copolymers having no hydrophobic macromonomers grafted to the backbone. (As known in the art, synthetic graft copolymerizations processes may produce a mixture of polymer molecules containing no, one, or more than one hydrophobic macromer covalently bonded to and pendant from the polymeric backbone. From knowledge of the amount and number average molecular weight of hydrophobic macromonomer in a polymer sample, and the number average molecular weight of the polymer sample, it is possible to calculate the average number of hydrophobic macromonomers per polymer backbone.) The hydrophilic polymeric backbone is hereinafter alternatively referred to as "polymeric backbone".

Unless otherwise state, as used herein "hydrophilic" mean that a material is substantially soluble in water, $C_2$–$C_3$ alcohols, or mixtures thereof, and "hydrophobic" means that a material is substantially insoluble in water, $C_2$–$C_3$ alcohols, or mixtures thereof. As used herein, hydrophilic, polymeric materials (e.g., a homopolymer or copolymer, including the polymeric backbone, macromonomers and graft copolymer of the present invention) are those which are soluble in distilled (or equivalent) water, ethanol, n-propanol, isopropanol, or mixtures thereof, at 25° C., at a concentration of 0.2% of the polymeric material by weight, and are more preferably soluble at 1.0% of the polymeric material by weight. As used herein, hydrophobic polymeric materials are those which are not soluble in distilled (or equivalent) water, ethanol, n-propanol, isopropanol, or mixtures thereof, at 25° C., at a concentration of 0.2% polymeric material by weight, and preferably not soluble at 0.1% polymeric material by weight. The weight average molecular weight of a polymeric material for purposes of determining such solubility or insolubility shall be about 40,000, although solubility at higher molecular weight shall also be indicative of solubility at about 40,000.

The graft copolymer should have a weight average molecular weight (in grams/mole) of at least about 20,000. There is no upper limit for molecular weight except that which limits applicability of the invention for practical reasons, such as processing, aesthetic characteristics, formulateability, etc. In general, the weight average molecular weight will be less than about 10,000,000, more generally less than about 5,000,000, and typically less than about 3,000,000. Preferably, the weight average molecular weight will be between about 50,000 and about 2,000,000, more preferably between about 75,000 and about 1,000,000, most preferably between about 75,000 and about 750,000.

Preferably, the graft copolymers hereof when dried to form a film have at least one $T_g$ or $T_m$ of at least about 10° C., more preferably at least about 20° C., so that they are not unduly sticky, or "tacky" to the touch. As used herein, the abbreviation "$T_g$" refers to a glass transition temperature of a material and the abbreviation "$T_m$" refers to the crystalline melting point of a material, if such a transition exists for a given material. The aforementioned $T_g$ and $T_m$ generally correspond to the $T_g$ or $T_m$ of the polymer comprising the polymeric backbone, when such a polymer is dried to a thin film. Methods of determining the $T_g$ and $T_m$ of thin films of polymeric materials are well known in the art and are applicable herein. An exemplary method is described in *Introduction of Polymer Science and Technology,* Herman S. Kaufman and Joseph J. Falcetta, eds., John Wiley and Sons, 1977, pp. 239–300, incorporated herein by reference.

The graft copolymers should satisfy the following four criteria:

(1) when dried the graft copolymer phase-separates into a discontinuous phase which includes the hydrophobic macromonomer(s) portion and a continuous phase which includes the polymeric backbone portion;

(2) the hydrophobic macromonomer(s) portion is covalently bonded to the polymeric backbone portion;

(3) the number average molecular weight of the hydrophobic macromonomer(s) portion is at least about 500; and (4) when used in a composition, such as a personal care composition for application to the hair or skin, the polymeric backbone portion should permit the graft copolymer to deposit on the intended surface, such as hair or skin.

Without intending to be limited by theory, it is believed that the phase separation property of the graft copolymer improves the mechanical performance of the copolymer, as reflected in a longer extension to break compared to the hydrophilic polymeric backbone, resulting in improved hair holding benefits. Phase separation properties of the graft copolymer can be determined by several methods as follows.

In one method, the polymer is cast as a solid film out of a solvent (i.e., a solvent which dissolves both the backbone and the graft portions). This film is then sectioned and examined by transmission electron microscopy. Microphase separation is demonstrated by the observation of inclusions in the continuous phase. These inclusions should have the proper size to match the size of the graft macromonomer chain (typically a few hundred nm or less) and the proper density to match the amount of macromonomer present. This behavior is well documented in the literature for polymers with this structure (see, for example. S. D. Smith, Ph.D. Thesis, University of Virginia, 1987, and references cited therein, said thesis incorporated by reference herein).

A second method for determining phase-separating characteristics involves examining the enrichment of the concentration of grafts at the surface of a polymer film relative to the concentration in the bulk polymer. Since the grafts prefer the low energy air interface, it preferentially orients on the polymer surface. This produces a surface with the grafts oriented at the surface of the film. This can be demonstrated experimentally by ESCA (electron spectroscopy for chemical analysis) of the dried film surface. Such an analysis shows a high level of grafts and a greatly reduced level of backbone polymer when the film surface is analyzed. (Surface here means the first few tens of Angstroms of film thickness.) By varying the angle of the interrogating beam the surface can be analyzed to varying depths.

The preferred graft copolymers hereof generally comprise from about 1% to about 50%, by weight, of hydrocarbon macromonomer units, i.e., macromonomer units (referred to herein as "C" monomers) which consist of a hydrocarbon polymer with one end of the polymer chain terminated with a group which can copolymerize with the monomers which polymerize to form the hydrophilic polymeric backbone, and from about 50% to about 99% by weight, of monomer units comprising said hydrophilic polymeric backbone.

The Polymeric Backbone

The monomer units comprising said hydrophilic polymeric backbone can be derived from hydrophilic monomers (alternatively referred to herein as "A" monomers) (typically polar monomers), or mixtures of such hydrophilic monomers with hydrophobic monomers (alternatively referred to herein as "B" monomers) (typically low polarity monomers). As used herein, "hydrophobic monomers" means monomers which form substantially water insoluble homopolymers; "hydrophilic monomers" means monomers which form homopolymers which are substantially water soluble.

The A and optional B monomer units are selected from copolymerizable monomers, preferably ethylenically unsaturated monomers. By "copolymerizable", as used herein, is meant a material can be reacted with another material (e.g., the A monomer, B monomer and C macromonomer) in a polymerization reaction using one or more conventional synthetic techniques, such as ionic emulsion, dispersion, Ziegler-Natta, free radical, group transfer or step growth polymerization. In the present invention, monomers and macromonomers that are copolymerizable using conventional free radical initiated techniques are preferred. The term "ethylenically unsaturated" is used herein to mean a material (including preferred A monomers, B monomers and C macromonomers) that contains at least one polymerizable carbon-carbon double bond (which can be mono-, di-, tri-, or tetra-substituted). The A monomers, B monomers and C macromonomers preferably consist of monomers that, when polymerized, form a saturated polymer.

A wide variety of A and B monomer units can be utilized in the present invention, including combinations of two of more monomers A, and, when used, combinations of two or more monomers B. The A and B monomers are selected to meet the requirements of the copolymer.

A Monomer Units

Nonlimiting classes of A monomers useful herein include hydrophilic monomers selected from the group consisting of unsaturated mono-, di and poly- carboxylic acids; (meth) acrylamides; (meth)acrylates; (meth)acrylate alcohols; organic acid anhydrides; esters of organic acid anhydrides; hydrophilic vinyl compounds; hydrophilic allyl compounds; hydrophilic imides; salts of any such compounds; and combinations thereof.

Representative examples of such hydrophilic monomers include acrylic acid, methacrylic acid, N,N-dimethylacrylamide, dimethylaminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (such as that produced by the hydrolysis of vinyl acetate after polymerization), vinyl caprolactam, salts of any acids and amines listed above, and combinations thereof.

Preferred hydrophilic monomers include acrylic acid, N,N-dimethyl acrylamide, dimethylaminoethyl methacrylate, quaternized dimethylaminoethyl methacrylate, vinyl pyrrolidone, salts of acids and amines listed above, and combinations thereof. The quaternized monomers can be quaternized either before or after the copolymerization with other monomers of the graft copolymer.

B Monomer Units

Nonlimiting classes of B monomers useful herein include hydrophobic monomers selected from the group consisting of acrylic acid esters; methacrylic acid esters; N-alkyl acrylamides; vinyl compounds, vinylidene compounds; unsaturated hydrocarbons (e.g., olefins, including straight chain, branched chain, and cycloaliphatic olefins and aromatic ethylenically unsaturated compounds); and combinations thereof.

Representative examples of such hydrophobic monomers include acrylic or methacrylic acid esters of $C_1$–$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol(2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octa decanol, and the like, the alcohols having from about 1–18 carbon atoms with the number of carbon atoms preferably being from about 1–12; dicyclopentenyl acrylate; 4-biphenyl acrylate; pentachlorophenyl acrylate 3,5-dimethyladamantyl acrylate; 3,5-dimethyladamentyl methacrylate; 4-methoxycarbonylphenyl methacrylate; trimethylsilyl methacrylate; styrene; alkyl substituted styrenes including alpha-methylstyrene and t-butylstyrene; vinyl esters, including vinyl acetate, vinyl neononanoate, vinyl pivalate and vinyl propionate; vinyl chloride; vinylidene chloride; vinyl toluene; alkyl vinyl ethers, including isobutyl vinyl ether and s-butyl vinyl ether; butadiene; cyclohexadiene; bicycloheptadiene; 2,3-dicarboxylmethyl-1,6-hexadiene; ethylene; propylene; indene; norbornylene; β-pinene; α-pinene; and combinations thereof.

Preferred hydrophobic B monomers are selected from the group consisting of acrylic or methacrylic acid esters of $C_1$–$C_{18}$ alcohols, styrene, alpha-methylstyrene, t-butylstyrene, polystyrene macromer, vinyl acetate, vinyl propionate, vinyl chloride, vinylidene chloride, vinyl toluene, butadiene, cyclohexadiene, ethylene, propylene, and combinations thereof. More preferably, the hydrophobic B monomers are selected from the group consisting of: n-butyl methacrylate, isobutyl methacrylate, t-butyl acrylate, t-butyl methacrylate, 2-ethylhexyl methacrylate, methyl methacrylate, and combinations thereof. Most preferably, the hydrophobic B monomers are selected from t-butyl acrylate, t-butyl methacrylate or combinations thereof.

As used herein, A and B monomers are meant to include monomers that are unsubstituted or substituted with one or more substituted groups. Exemplary substituent groups include, but are not limited to, alkyl, aryl, carboxyl, halo groups, and combinations thereof.

Hydrophobic C Macromonomer Units

The hydrophobic macromonomers (C monomers) are derived from hydrophobic monomers such that the polymeric material of the macromonomer is hydrophobic and such that a thin film of such material has a Tg of less than about 0° C., more preferably less than about −25° C. Thus, the hydrophobic macromonomers comprise hydrophobic monomers which form a homo- or co- polymer having a Tg of about 0° C. or less, preferably about −25° C. or less. The hydrophobic macromonomer should have a weight average molecular weight of at least about 500, preferably from about 1,000 to about 200,000, more preferably from about 1500 to about 30,000, most preferably about 5,000 to about 25,000.

The hydrophobic C macromonomer units of the present invention are large polymeric building blocks containing repeating structural units. The C macromonomers can be formed from the polymerization of smaller monomer units. The C macromonomers encompass a wide variety of structures and are copolymerizable with the A and B monomer units. Without intending to be limited by theory, the hydrophobic C macromonomer units are believed to contribute to the overall solubility properties of the copolymers.

Either a single type of C macromonomer or combinations of two or more C macromonomers can be utilized, so long as the requirements of the copolymer are met. Also, each C macromonomer can be constructed from two or more randomly repeating monomer units, in which case the macromonomer would actually be considered a copolymer type of macromonomer. In any event, the C macromonomers are selected to meet the requirements of the graft copolymers. The hydrophobic macromonomers contain hydrophobic monomer units and optionally hydrophilic monomer units.

C macromonomers that are useful herein contain a polymeric portion and a copolymerizable moiety, preferably an ethylenically unsaturated moiety, that is copolymerizable with the A and B units. The polymeric portion of the C macromonomers has a carbon based main chain, which may be substituted or unsubstituted with a variety of one or more functional groups, e.g., alkyl, aryl, carboxyl, halo. Typically, the preferred C macromonomers are those that are endcapped with the ethylenically unsaturated moiety. By "endcapped" as used herein is meant that the ethylenically unsaturated moiety is at or near a terminal position of the C macromonomer. However, this definition of "endcapped" is not intended to limit the macromonomer to only those macromonomers which terminate in a carbon-carbon double bond (whether mono-, di-, tri-, or tetra-substituted).

The hydrophobic C macromonomers of the present invention can be synthesized utilizing a variety of standard synthetic procedures familiar to the polymer chemist of ordinary skill in the art. Furthermore, these macromonomers can be synthesized starting from commercially available polymers.

For example, the hydrophobic C macromonomers can be synthesized by the polymerization (acid, base, free radical, or auto-initiated) of one or more hydrophobic monomers, and optionally hydrophilic monomers, to form a polymer which is subsequently reacted with or "endcapped" with a copolymerizable structural unit E, preferably an ethylenically unsaturated moiety. Alternatively, the C macromonomers can be synthesized starting with commercially available hydrophobic polymers which are "endcapped" with the structural unit referred to herein as E. In yet another alternative, the C macromonomer can be synthesized by starting with the structural unit E, and polymerizing onto it the desired hydrophobic monomer units. It is to be understood that in this third alternative, the ethylenically unsaturated moiety of the E unit is not consumed in the synthesis but its integrity is preserved for subsequent copolymerization of the C macromonomer with the A units. All of the synthetic alternatives are merely illustrative in that any other suitable synthetic procedures can be utilized to prepare the C macromonomers and copolymers of the present invention.

The C macromonomer is at least one hydrophobic macromonomer unit copolymerizable with A and B, corresponding to the formula (I) or (II):

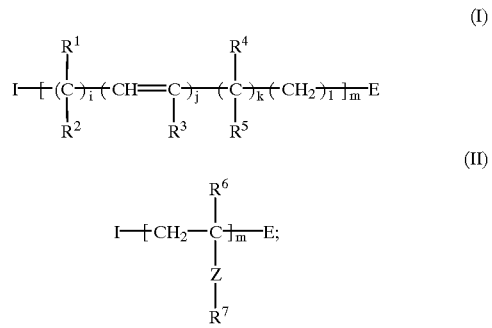

wherein:
$R^1$, $R^2$, $R^3$, $R^4$ and $R^5$ are, independently, H or $C_1$ to $C_5$ straight or branched alkyl group;
$R^6$=H or $C_1$ to $C_8$ alkyl;
$R^7$=$C_4$ to $C_{18}$;

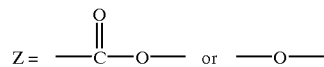

i and k are, independently, an integer of about 1 or greater;
j and l are, independently, an integer of about 0 or greater;
m is an integer from 10 about 2000, preferably from about 15 to 300, and more preferably from about 20 to about 250; and E and I are as defined herein.

E is an ethylenically unsaturated "endcapping" group that is copolymerizable with the A and optional B monomer units. Preferably E is selected from the group consisting of acrylamide, methacrylamide, vinyl, allyl, acryloyl, methacryloyl, ethacryloyl, 2-vinylbenzyl, 3-vinylbenzyl, 4-vinylbenzyl, 2-vinylbenzoyl, 3-vinylbenzoyl, 4-vinylbenzoyl, 1-butenyl, 1-propenyl, isobutenyl, isoprenyl, cyclohexenyl, cyclopentenyl, and combinations thereof. Even more preferred is when E is selected from the group consisting of vinyl, allyl, acryloyl, methacryloyl, ethacryloyl, 3-vinylbenzyl, 4-vinylbenzyl, 3-vinylbenzoyl, 4-vinylbenzoyl, 1-butenyl, 1-propenyl, isobutenyl, and combinations thereof. Most preferred is when E is selected from the group consisting of vinyl, allyl, acryloyl, methacryloyl, ethacryloyl, 3-vinylbenzyl, 4-vinylbenzyl, and combinations thereof.

I is a chemical initiator moiety. Without being limited by theory, I can be derived from a chemical initiator or solvent used in the synthesis of the C macromonomer. Nonlimiting examples of such initiators from which I can be derived include hydrogen ion, hydrogen radical, hydride ion, hydroxide ion, hydroxyl radical, peroxide radical, peroxide anion, C1–20 carbocations, C1–20 carbanions (e.g., sec-butyl carbanions, and 1,1-diphenyl-4-methylpentyl carbanion), C1–20 carbon radicals, C1–20 aliphatic and aromatic alkoxy anions, ammonium ion, substituted ammonium ions (e.g., C1–20 alkyl and C1–20 alkoxy substituted), and C1–20 carbocations (e.g., cumyl carbocation). I can be derived from any useful solvent, nonlimiting examples of which include water, methanol ethanol, propanol, isopropanol, acetone, hexane, dichloromethane, chloroform, benzene, and toluene. Nonlimiting examples of I include chemical moieties selected from the group consisting of hydrogen, C1–40 straight or branched chain alkyl, benzyl, 1-phenyl substituted C2–40 straight or branched chain alkyl, 1,1-diphenyl substituted C2–40 straight or branched chain alkyl, and combinations thereof. More preferably I is selected from the group consisting of 1,1-diphenyl-4-methylpentyl, sec-butyl, and cumyl. Most preferably I is sec-butyl or cumyl.

$R^1$, $R^2$, $R^3$, $R^4$ and $R^5$ are suitably independently derived from monomer units such as those described in reference to the A and B monomer units, preferably monomers selected from the group consisting of ethylenically unsaturated, straight or branched hydrocarbons and ethylenically unsaturated esters of acrylic acid and methacrylic acid. More preferred such monomers are hydrocarbons selected from isobutylene, butadiene, isoprene, 1-butene, 5-methyl-1-hexene, 6-methyl-1-heptene, 4,4-dimethyl-1-pentene etc.; esters of acrylic acid and an alcohol selected from n-butyl, dodecyl, 2-ethylhexyl, 2-ethylbutyl, n-ethyl, n-heptyl, n-hexyl, iso-butyl, iso-decyl, iso-propyl, 3-methylbutyl, 2-methylpentyl, nonyl, octyl, and propyl alcohol; and esters of methacrylic acid and an alcohol selected from dodecyl, 2-ethylhexyl, hexyl, decyl, octadecyl, octyl, n-pentyl and tridecyl alcohol.

Nonlimiting examples of these endcapped hydrophobic macromonomers include acryloyl, methacryloyl, or 2-,3- or 4-vinyl benzyl endcapped polymers of methacrylic or acrylic acid esters, such as, poly(n-butyl acrylate), poly(dodecyl acrylate), poly(2-ethylhexyl acrylate), poly(2-ethylbutyl acrylate), poly(n-ethyl acrylate), poly(n-heptyl acrylate), poly(n-hexyl acrylate), poly(iso-butyl acrylate), poly(iso-decyl acrylate), poly(iso-propyl acrylate), poly(3-methylbutyl acrylate), poly(2-methylpentyl acrylate), poly(nonyl acrylate), poly(octyl acrylate), poly (2-ethylhexyl methacrylate), poly(tridecyl methacrylate), poly(n-pentyl methacrylate), poly(octyl methacrylate), poly(octadecyl methacrylate), poly(dodecyl methacrylate), poly(n-pentyl methacrylate). Other examples include, methacryloyl, acryloyl or 2-,3-, or 4- vinyl benzyl endcapped polymers of poly(isobutylene), poly(isoprene), hydrogenated poly(1,2-butadiene), hydrogenated poly(1,4-butadiene), hydrogenated poly(isoprene), poly(1,2-butadiene), poly(1-butene), poly(5-methyl-1-hexene), poly(6-methyl-1-heptene), poly (4,4-dimethyl-1-pentene), and poly(iso-butyl vinyl ether).

Examples of other macromonomers include "copolymer"type C macromonomers containing two or more randomly repeating monomer units. Nonlimiting examples of these "copolymer" type of macromonomers include acryloyl endcapped poly[4-t-butyl vinyl benzene-co-2-ethylhexyl acrylate], poly[2-ethylhexyl acrylate-co-octyl acrylamide), poly[2-ethyl vinyl benzene-co-octyl methacrylate)], and the like.

The endcapped hydrophobic macromonomers can be synthesized using standard synthetic procedures which involve polymerizing, usually under cationic or anionic initiation conditions, the appropriate monomer unit, (e.g., isobutylene, 1,3-butadiene, isoprene etc.). A wide variety of initiating systems can be used, nonlimiting examples of which include cationic initiators, such as cumyl acetate/$TiCl_4$, cumyl methyl ether/$BCl_3$; and anionic initiators such as n-butyl lithium, sec-butyl lithium, t-butyl lithium, lithium aluminum hydride, sodium hydride, and the like. Nonlimiting examples of these initiating systems are provided in Designed Polymers by *Carbocationic Macromolecular Engineering, Theory and Practice,* J. P. Kennedy and B. Ivan, Chapter II, p.5, Hanser Publishers, N.Y. (1991), and in *Anionic Polymerization: Principles and Practice,* Maurice Morton, Chapter 2, p. 13, Academic Press, N.Y. (1983).

In the case of cationic polymerization, once the desired degree of polymerization is complete the polymer is isolated and further derivatized to obtain vinyl benzyl, methacryloyl or acryloyl end capped polymer. A nonlimiting example of macromonomer synthesized by cationic polymerization is poly(isobutylene). In the case of anionic polymerization, once the desired degree of polymerization is achieved, an appropriate endcapping reagent is typically used to terminate the polymerization and to endcap the macromonomer. Nonlimiting examples of these endcapping reagents include 2-vinylbenzyl chloride, 3-vinylbenzyl chloride, 4-vinylbenzyl chloride, and the like. Alternatively, the endcapping can be achieved by reacting the polymeric reaction mixture with one equivalent of ethylene oxide to terminate the polymer with a —$CH_2CH_2$—O— moiety, followed by reaction with an endcapping reagent such as an unsaturated acid halide.

The grafts are alternatively derived from monomers selected from the group consisting of ethylenically unsaturated, straight or branched hydrocarbons and ethylenically unsaturated esters of acrylic acid and methacrylic acid. More preferred monomers which comprise the grafts are hydrocarbons selected from isobutylene, butadiene, isoprene, 1-butene, 5-methyl-1-hexene, 6-methyl-1-heptene, 4,4-dimethyl-1-pentene etc.; esters of acrylic acid and an alcohol selected from n-butyl, dodecyl, 2-ethylhexyl, 2-ethylbutyl, n-ethyl, n-heptyl, n-hexyl, iso-butyl, iso-decyl, iso-propyl, 3-methylbutyl, 2-methylpentyl, nonyl, octyl, and propyl alcohol; and esters of methacrylic acid and an alcohol selected from dodecyl, 2-ethylhexyl, hexyl, decyl, hexyl, octadecyl, octyl, n-pentyl, and tridecyl alcohol.

Preferred Graft Copolymers

The particular relative amounts of A, B, and C monomers can vary as long as the hydrophilic polymeric backbone is soluble in the hydrophilic solvent hereof, and the graft copolymer exhibits phase separation when dried. The composition of any particular graft copolymer will help determine its formulation properties. In fact, by appropriate selection and combination of particular A, B and C monomers, the copolymer can be optimized for inclusion in specific vehicles.

In general, the graft copolymer will preferably comprise from about 50% to about 99%, more preferably from about 60% to about 98%, most preferably from about 75% to about 95%, by weight of the copolymer, of monomer units comprising the hydrophilic polymeric backbone, e.g., the total A and B monomer units, and from about 1% to about 50%, preferably from about 2% to about 40%, more preferably from about 5% to about 25%, of monomers comprising the hydrophobic macromonomer(s), e.g. the C macromonomer units. For example, the level of hydrophilic A monomer units in the polymer backbone can be from about 10% to about 100%, preferably from about 15% to about 80%, more preferably from about 15% to about 50%, most preferably from about 15% to about 40%; and the level of hydrophobic B monomer units in the polymer backbone can be from 0% to about 90%, preferably from about 20% to about 85%, more preferably from about 50% to about 85%, most preferably from about 60% to about 85%.

The polymeric backbone of the graft copolymer included in the composition hereof must be soluble in the hydrophilic solvent, which is hereinafter referred to as the graft copolymer, as a whole, being soluble in the hydrophilic solvent. This is determined according to whether the polymer can stay in solution or precipitates out of solution at 25° C. at the concentration present in the composition or the range of concentrations for the graft copolymer described herein. It is well within the skill of one in the art to select monomers for incorporation into the copolymers for formulateability and solubility in selected hydrophilic solvent systems.

For example, copolymers which are soluble in an aqueous formulation preferably have the composition: from about 30% to about 98% (more preferably from about 30% to about 80%) monomer A, from about 0% to about 70% (more preferably from about 5% to about 70%) monomer B, and from about 1% to about 40% macromonomer C.

Exemplary graft copolymers for use in the present invention include the following, where the composition is given as weight part of monomer used in the synthetic.
Poly[poly(acrylic acid/t-butylacrylate)-graft-poly (isobutylene) macromonomer] (10,000 Mn) (20/65/15 w/w/w) Polymer weight average molecular weight of 120,000;
Poly[poly(dimethylaminopropyl methacrylate/t-butylacrylate)-graft-poly(ethylhexyl methacrylate) macromonomer] (12,000 Mn) (25/60/15 w/w/w) Polymer weight average molecular weight of 200,000;
Poly[poly(acrylic acid/t-butyl acrylamide/t-butylacrylate)-graft-poly(isobutylene) macromonomer] (15,000 Mn) (10/40/40/10 w/w/w/w) Polymer molecular weight 100,000.

Methods of making graft copolymers are well known in the art and are applicable to the present invention. For example, suitable methods are described in detail in "*Block and Graft Polymerization,* R. J. Ceresa, ed., John Wiley and Sons, 1973, and "*Principles of Polymerization,* 3rd ed." George Odian, John Wiley and Sons, 1991. In general, the hydrophobic macromonomers can be substituted on the polymer backbone or can be made by co-polymerization of suitable polymerizable monomers.

Thus, the graft copolymers can be synthesized by free radical polymerization of the A, B, and C monomers. The general principles of free radical polymerization methods are well understood. See, for example, Odian, "Principles of Polymerization", 2nd edition, John Wiley & Sons, 1981, pp. 179–318. The desired monomers are all placed in a reactor, along with a sufficient amount of a mutual solvent so that when the reaction is complete the viscosity of the reaction is reasonable. Typical monomer loadings are from about 20% to about 50%. Undesired terminators, especially oxygen, are removed as needed. This is done by evacuation or by purging with an inert gas, such as argon or nitrogen. The initiator is introduced and the reaction brought to the temperature needed for initiation to occur, assuming thermal initiators are used. Alternatively, redox or radiation initiation can be used. The polymerization is allowed to proceed as long as needed for a high level of conversion to be achieved, typically from a few hours to a few days. The solvent is then removed, usually by evaporation or by precipitating the polymer by addition of a nonsolvent. The polymer can be further purified, as desired.

In particular, the graft copolymers can be purified by removing unreacted monomer and graft copolymer with viscosities at 25° C. of about 10,000,000 centistokes and less. This can be done, for the example, by hexane extraction. After drying the resin from its reaction solvent hexane extraction of the reaction product can be performed by adding an excess of hexane to the reaction product and heating to near the Tg of the backbone portion of the polymer. The mixture is held at this temperature with stirring for about 30 minutes and cooled to room temperature. The hexane is removed by vacuum suction. Two more hexane extraction cycles are preferably conducted in the same manner as above. After the third cycle, residual hexane remaining with the product is removed by distillation and vacuum drying.

As an alternative to a batch reaction, the graft copolymer can be made by a semi-continuous or continuous process. In the semi-continuous process, two or more additions of monomers is made during the polymerization reaction. This is advantageous when the polymer is made of several monomers which react during the polymerization at different rates. The proportions of monomers added to the reaction at the separate points of addition can be adjusted by one of ordinary skill in the art such that the polymers of the final product have a more uniform structure. In other words, the polymers of the final product will have a more consistent monomer content distribution for each of the monomer types charged to the reaction. Typically, the hydrophobic macromonomers (C monomers) will react more slowly than the A and B monomers which comprise the polymer backbone.

As is known in the art, polymers which have acidic functionalities, such as carboxyl groups, are usually used in at least partially neutralized form to promote solubility/dispersibility of the polymer. In addition, use of the neutralized form aids in the ability of the hair styling compositions to be removed from the hair by shampooing. In general, it is preferred that from about 10% to 100%, more preferably from about 20% to about 90%, even more preferably from about 40% to about 85%, of the acidic monomers of the polymer be neutralized.

Any conventionally used base, including organic or inorganic (metallic or other) bases, may be used for neutralization of the polymers. Metallic bases are particularly useful in the present compositions. Hydroxide, where the cation is ammonium, an alkali metal or an alkaline earth metal, are suitable neutralizers for use in the present hair spray compositions. Preferred neutralizing agents for use in hair spray compositions of the present invention are potassium hydroxide and sodium hydroxide. Examples of other suitable neutralizing agents which may be included in the hair spray compositions of the present invention include amines, especially amino alcohols such as 2-amino-2-methyl-1,3-propanediol (AMPD), 2-amino-2-ethyl-1,3-ropanediol (AEPD), 2-mino-2-methyl-1-propanol (AMP), 2-amino-1-butanol (AB), monoethanolamine (MEA), diethanolamine (DEA), triethanolamine (TEA), monosiopropanolamine (MIPA), diisopropanolamine (DIPA), triisopropanolamine (TIPA) and dimethyl stearamine (DMS). Particularly useful neutralizing agents are mixture of amines and metallic bases.

Polymers having basic functionalities, e.g., amino groups, are preferably at least partially neutralized with an acid, e.g., hydrogen chloride.

Neutralization can be accomplished by techniques well known in the art, and before or after polymerization of the monomers comprising the graft copolymer.

Solubility of the graft copolymer, as described above, should be determined after neutralization, if any, as well as after addition of other ingredients that may be included in the hydrophilic solvent phase, such as surfactants, solubilizers, etc.

Carrier Phase

The hair styling compositions of the present invention also include a carrier phase, preferably hydrophilic, as a liquid vehicle for the graft copolymer. The graft copolymer is substantially soluble or dispersible in the carrier phase. The carrier phase is present in the hair styling compositions at a level of from about 85% to about 99.9%, preferably from about 85% to about 98%, more preferably from about 90% to about 98% of the total composition.

The carrier phase comprises a hydrophilic solvent, which is preferably present in the hair styling compositions at a level of from about 20% to about 99.9%, more preferably from about 40% to about 98%, most preferably from about 60% to about 98% of the total composition. Suitable hydrophilic solvents are those in which the graft copolymer is substantially soluble. Preferably, the graft copolymer is soluble in the solvent at 25° C., at a concentration of 0.2% of the copolymer by weight, and are more preferably soluble at 1.0% of the copolymer by weight.

The hydrophilic solvents essential to the present compositions comprise one or more polar solvents, preferably selected from the group consisting of water, $C_2$–$C_3$ monohydric alkanols, and mixtures thereof. If present, $C_3$ alkanols, such as isopropanol, are preferably used at levels no greater than about 15% by weight of the composition, more preferably no greater than about 12%, most preferably no greater than about 10%. High levels of $C_3$ monohydric alcohols are undesirable in the present compositions due to potential odor issues they can create. Preferred hydrophilic solvent phases contain water, ethanol, or mixtures thereof.

Where water and alcohol mixtures are used, for instance, water-ethanol or water-isopropanol-ethanol, the water content of the compositions is generally in the range of from about 0.5% to about 99%, preferably from about 5% to about 50% by weight of the total composition. In such mixtures, the alcohol solvents are generally present in the range of from 0.5% to about 99%, preferably from about 50% to about 95%, by weight of the total composition.

In yet another aspect of this invention are provided hair styling products, such as hair spray compositions, which contain reduced levels of volatile organic compounds such as solvents. As used herein, "volatile organic compounds" or "VOC" are those organic compounds that contain less than 12 carbon atoms or have a vapor pressure greater than 0.1 mm of mercury. A reduced volatile organic compound hair spray composition of the present invention contains no more than 80% volatile organic compounds (which include, for example, alkanols but not water).

In the reduced volatile organic compound hair styling compositions hereof, the compositions generally comprise at least 10%, by weight, of water. It is also specifically contemplated that they may contain at least about 11%, 12%, 13%, 14%, 15%, or more water.

Exemplary reduced volatile organic compound hair styling compositions hereof will comprise up to about 90%, preferably up to about 70%, more preferably up to about 60%, even more preferably no more than about 50%, water; and from about 10% to about 80%, preferably from about 20% to about 80%, more preferably from about 40% to about 80%, of volatile organic compounds. It is also contemplated that the compositions can be limited to containing no more than about 75%, 65%, 55%, or other levels of volatile organic compounds.

Optional Ingredients

The compositions hereof may contain as an optional element a volatile, hydrophobic, branched chain hydrocarbon. The branched chain hydrocarbon hereof, if used, is present at a level of from about 0.5% to about 15%, preferably from about 1% to about 10%, more preferably from about 2% to about 8%, by weight of the composition.

The branched chain hydrocarbon is characterized by a boiling point of at least about 105° C., preferably at least about 110° C., more preferably at least about 125° C., most preferably at least about 150° C. The boiling point is also generally about 260° C., or less, preferably about 200° C. or less. The hydrocarbon chosen should also be safe for topical application to the hair and skin. Thus, the hydrocarbon is preferably generally recognized as not being toxic or unacceptably irritating.

Preferred branched chain hydrocarbons are selected from the group consisting of $C_{10}$–$C_{16}$ branched chain hydrocarbons, and mixtures thereof, more preferably $C_{10}$–$C_{14}$ branched chain hydrocarbons, even more preferably $C_{11}$–$C_{13}$ branched chain hydrocarbons, most preferably $C_{12}$ branched chain hydrocarbons. Saturated hydrocarbons are preferred, although it is not intended to exclude unsaturated hydrocarbons.

Examples of suitable branched chain hydrocarbons include isoparaffins of the above chain sizes. Isoparaffins are commercially available from Exxon Chemical Co. Examples include Isopar™ G ($C_{10}$–$C_{11}$ isoparaffins), Isopar™ H and K ($C_{11}$–$C_{12}$ isoparaffins), and Isopar™ L ($C_{11}$–$C_{13}$ isoparaffins). Most preferred are $C_{12}$ branched chain hydrocarbons, especially isododecane. Isododecane is commercially available from Preperse, Inc. (South Plainfield, N.J., USA) as Permethyl™ 99A.

Without intending to be necessarily limited by any particular theory, it is believed that the branched chain hydrocarbon solubilizes the hydrophobic macromonomer portion of the graft copolymer. This is believed to aid in obtaining a smoother polymer film upon drying. Since the hydrocarbon is less volatile than the hydrophilic solvent phase, the hydrocarbon maintains the hydrophobic macromonomer portions in solubilized form for a relatively long period as the compositions dries, thus minimizing aggregation of the hydrophobic macromonomer portions and, therefore, allowing the polymer to dry as a smoother film.

Solubility of the hydrophobic macromonomer portion of the graft copolymer in the hydrocarbon can be easily determined by verifying whether a hydrophobic macromonomer of the same composition and molecular weight as that grafted to the graft copolymer is soluble in the hydrocarbon. Preferably, the macromonomer is soluble at 25° C. at a concentration of 0.1% by weight of the hydrocarbon, preferably at 1%, more preferably at 5%, most preferably at 15%.

The hydrocarbon, however, is insoluble in the hydrophilic solvent of the composition. This is determined in the absence of the graft copolymer, or other emulsifying agents, and can easily be verified by observing whether the hydrophilic solvent and the hydrocarbon form separate phases after being mixed together at room temperature.

The compositions hereof can optionally contain a plasticizer for the graft copolymer. Any plasticizer suitable for use in hair care products or for topical application to the hair or skin can be used. A wide variety of plasticizers are known in the art. These include glycerin, diisobutyl adipate, butyl stearate, propylene glycol, tri-$C_2$–$C_8$ alkyl citrates, including triethyl citrate and tripropyl, -butyl, -pentyl, etc., analogues of triethyl citrate. Triethyl citrate is preferred.

Plasticizers are typically used at levels of from about 0.01% to about 10%, by weight of the composition, preferably from about 0.05% to about 3%, more preferably from about 0.05% to about 1%. Preferably, the weight ratio of graft copolymer to the plasticizer is from about 1:1 to about 40:1, preferably from about 10:1 to 30:1, more preferably from about 15:1 to about 25:1.

Optionally, the compositions of the present invention can contain an effective amount of a non-surface active ionic strength modifier system for reducing the viscosity of the hair spray composition. When used, the ionic strength modifiers will be present in the present compositions at a level of at least about 0.01%, by weight of the composition. The upper limit is dependent upon the maximum amount of the ionic strength modifiers that can be present in the particular compositions hereof such that the hair setting resin remains solubilized or dispersed. As will be understood by those skilled in the art, as the ionic strength of the composition is increased, the resin will eventually fall out of solution, or otherwise no longer remain solubilized or dispersed in the hydrophilic liquid carrier. The upper limit of the ionic strength modifier system level will vary depending upon the particular ionic strength modifiers, liquid vehicle, resin, and other ingredients present in the composition. Thus, for example, the maximum amount of the ionic strength modifiers that can be used will tend to be lower for compositions with liquid vehicles containing less water, compared to compositions with more water. Generally, the compositions will comprise about 4%, by weight, or less of the ionic strength modifiers, more generally about 2% or less, and typically about 1% or less. Preferably, the compositions hereof will comprise from about 0.01% to about 0.5%, more preferably from about 0.01% to about 0.1%, of the ionic strength modifier system.

The ionic strength modifier system comprises a mixture of monomeric cations and anions. The ions of the ionic strength modifier system hereof are non-surface active, i.e. they do not significantly reduce surface tension. For purposes hereof, non-surface active shall mean the ions, which at a 0.5% aqueous solution concentration, reduce surface tension by no more than 5.0 dynes/cm2. Generally, the ions of the ionic strength modifier system hereof will be characterized by having, at maximum, four or less carbon atoms per charge, preferably two or less carbon atoms, in any aliphatic chain or straight or branched chain organic heterochain.

The ionic strength modifier system comprises monomeric ions of the type which are products of acid-base reactions. Thus, basic and acidic ions OH$^-$ and H$^+$ do not constitute part of the ionic strength modifier system hereof, although they may be present in the composition. The ions hereof are incorporated into the composition in a form such that they can exist in the composition as free ions, i.e., in dissociated form. It is not necessary that all of the ions added exist in the composition as free ions, but must be at least partially soluble or dissociated in the composition. The ionic strength modifiers can be incorporated into the hair styling compositions, for example, by addition of soluble salts, or by addition of mixtures of acids and bases, or by a combination thereof. It is a necessary aspect of the invention that both anions and cations of the ionic strength modifier system be included in the composition.

Suitable cations for use include, for example, alkali metals, such as lithium, sodium, and potassium, and alkaline-earth metals, such as magnesium, calcium, and strontium. Preferred of the divalent cations is magnesium. Preferred monovalent metal ions are lithium, sodium, and potassium, particularly sodium and potassium. Suitable means of addition to the compositions hereof include, for example, addition as bases, e.g., hydroxides, sodium hydroxide and potassium hydroxide, and such as salts that are soluble in the liquid carrier, e.g. salts of monomeric anions such as those described below.

Other suitable cations include organic ions, such as quaternary ammonium ions and cationic amines, such as ammonium mono-, di-, and tri-ethanolamines, triethylamine, morpholine, aminomethylpropanol (AMP), aminoethylpropanediol, etc. Ammonium and the amines are preferably provided in the forms of salts, such as hydrochloride salts.

Monomeric anions that can be used include halogen ions, such as chloride, fluoride, bromide, and iodide, particularly chloride, sulfate, ethyl sulfate, methyl sulfate, cyclohexyl sulfamate, thiosulfate, toluene sulfonate, xylene sulfonate, citrate, nitrate, bicarbonate, adipate, succinate, saccharinate, benzoate, lactate, borate, isethionate, tartrate, and other monomeric anions that can exist in dissociated form in the hair styling composition. The anions can be added to the compositions hereof, for example, in the form of acids or salts which are at least partially soluble in the liquid vehicle, e.g., sodium or potassium salts of acetate, citrate, nitrate, chloride, sulfate, etc. Preferably, such salts are entirely soluble in the vehicle.

The use of ionic strength modifiers are especially useful in reduced volatile organic solvent compositions.

The present compositions can contain a wide variety of other optional ingredients, including among them any of the types of ingredients known in the art for use in hair care compositions, especially hair setting compositions such as especially hair spray compositions and hair setting tonics. Generally, such other adjuvants collectively can comprise from about 0.05% to about 5% by weight and preferably from about 0.1% to about 3%, by weight. Such conventional optional adjuvants are well known to those skilled in the art and include, but are not limited to, surfactants (which may be anionic, cationic, amphoteric, or zwitterionic and which include fluorinated surfactants and silicone copolyols), propellants, hair conditioning agents (e.g., silicone fluids, fatty esters, fatty alcohols, long chain hydrocarbons, cationic surfactants, etc.); emollients; lubricants and penetrants such as various lanolin compounds; protein hydrolysates and other protein derivatives; ethylene adducts and polyoxyethylene cholesterol; dyes, tints, bleaches, reducing agents and other colorants; pH adjusting agents; sunscreens; preservatives; thickening agents (e.g. polymeric thickeners, such as xanthan gum); and perfume.

Hair Styling Compositions

The present invention encompasses a wide variety of hair styling compositions, including hair spray compositions, mousses, and hair setting tonics. In general, the compositions will be flowable, low viscosity compositions that, preferably, are suitable for spray application. Higher viscosity compositions are also contemplated, however.

Hair spray compositions and mousses of the present invention can be dispensed from containers which are aerosol dispensers or pump spray dispensers. Such dispensers, i.e., containers, are well known to those skilled in the art and are commercially available from a variety of manufacturers, including American National Can Corp. and Continental Can Corp.

When the hair spray compositions are to be dispensed from a pressurized aerosol container, a propellant which consists of one or more of the conventionally-known aerosol propellants may be used to propel the compositions. A suitable propellant for use can be generally any liquifiable gas conventionally used for aerosol containers.

Suitable propellants for use are volatile hydrocarbon propellant which can include liquified lower hydrocarbons of 3 to 4 carbon atoms such as propane, butane and isobutane. Other suitable propellants are hydrofluorocarbons such as 1,2-difluoroethane (Hydrofluorocarbon 152A) supplied as Dymel 152A by DuPont. Other examples of propellants are dimethylether, nitrogen, carbon dioxide, nitrous oxide and atmospheric gas.

The hydrocarbons, particularly isobutane, used singly or admixed with other hydrocarbons are preferred.

The aerosol propellant may be mixed with the present compositions and the amount of propellant to be mixed is governed by normal factors well known in the aerosol art. Generally, for liquifiable propellants, the level of propellant is from about 10% to about 60% by weight of the total composition, preferably from about 15% to about 50% by weight of the total composition.

Alternatively, pressurized aerosol dispensers can be used where the propellant is separated from contact with the hair spray composition such as a two component can of the type sold under the tradename SEPRO from American National Can Corp.

Other suitable aerosol dispensers are those characterized by the propellant being compressed air which can be filled into the dispenser by means of a pump or equivalent device prior to use. Such dispensers are described in U.S. Pat. Nos. 4,077,441, Mar. 7, 1978, Olofsson and 4,850,577, Jul. 25, 1989, TerStege, both incorporated by reference herein, and in U.S. Ser. No. 07/839,648, Gosselin et al., filed Feb. 21, 1992, also incorporated by reference herein. Compressed air aerosol containers suitable for use are also currently marketed by The Procter & Gamble Company under their tradename VIDAL SASSOON AIRSPRAY® hair sprays.

Conventional non-aerosol pump spray dispensers, i.e., atomizers, can also be used.

Other hair styling compositions include tonics and lotions, which are typically dispensed in a conventional bottle or tube, and applied directly to the hair or first dispensed to the hand and then to the hair.

Method of Making

The hair styling compositions of the present invention can be made using conventional formulation and mixing techniques. Preferably, a premixture of the graft copolymer and the hydrophilic solvent, preferably ethanol, is made first. If ethanol is not to be used in the composition, a premix of the graft copolymer with $C_3$ alkanol or water is typically employed. The other ingredients can then be added with mixing to provide a homogeneous mixture. It the polymer is neutralized, the neutralizer is preferably added to the premix prior to addition of other ingredients.

Method of Use

The compositions of the present invention are used in conventional ways to provide the hair styling/holding benefits of the present invention. Such methods generally involve application of an effective amount of the product to dry, slightly damp, or wet hair before and/or after the hair is arranged to a desired style. The composition is then dried or allowed to dry. By "effective amount" is meant an amount sufficient to provide the hair hold and style benefits desired considering the length and texture of the hair. In general, from about 0.5 g to about 30 g of product will be applied to the hair, depending upon the particular product formulation, dispenser type, length of hair, and type of hair style.

The following Experimentals and Examples further illustrate embodiments within the scope of the present invention. They are given solely for the purposes of illustration and are not to be construed as limitations of the present invention as many variations of the invention are possible without departing from its spirit and scope.

EXPERIMENTALS

The following synthesis exemplifies graft copolymers useful in the present compositions.

Experimental 1

Synthesis of Acryloyl Encapped Polyisobutylene Macromonomer

Prepare a solution of 100 grams (0.024 mol) hydroxy encapped polyisobutylene polymer (PIB-OH) having a weight average molecular weight of 4,172 g/mol by conventional living carbocationic polymerization of isobutylene (for example, as described in G. Kaszas, Poly. Bull., 20, 413 (1989). Add a two fold mole excess (4.84 g, 0.048 mol) triethylamine to the solution. Add this solution dropwise to a solution of acryloyl chloride (4.35 g, 0.048 mol) in dry methylene chloride (100 g) at 0° C. Stir for about 12 hours at room temperature, filter the mixture and evaporate the excess triethylamine and methylene chloride to obtain acryloyl endcapped polyisobutylene macromonomer.

Experimental 2

Batch Synthesis

Place 20 parts acrylic acid, 60 parts t-butyl acrylate, and 20 parts polyisobutylene macromonomer (10,000 MW) from Experimental 1 in a flask. Add sufficient tetrahydrofuran as the reaction solvent to produce a final monomer concentration of 20%. Purge the vessel with an inert atmosphere, preferably nitrogen or argon. Add initiator, (2,2'-azobisisobutyronitrile) to a level appropriate for the desired molecular weight. Typically this is in the range of 0.5% to 1.0% by weight relative to the amount of monomer. Heat to 60° C. and maintain this temperature for 48 hours while agitating. Terminate the reaction by cooling to room temperature. The polymer is purified by drying off the reaction solvent in an oven, or if acetone is used as the solvent precipitating the polymer, by adding water and then drying the precipitate.

Experimental 3

Semi-Continuous Synthesis

Place 20 parts acrylic acid, 60 parts t-butyl acrylate, and 30 parts polyisobutylene macromonomer (10,000 MW) from Experimental 1 in a flask. Add 300 parts tetrahydrofuran as the reaction solvent to produce a final monomer concentration of 20%. Purge the vessel with an inert atmosphere, e.g., nitrogen or argon. Add initiator, (2,2'- azobisisobutyronitrile) as in Experimental 2. Heat to 60° C. and maintain this temperature. After polymerization of these monomers has proceeded about 15 minutes to about 1 hour, e.g. about 30 minutes, add a second monomer charge of 20 parts acrylic acid and 60 parts t-butyl acrylate, to give a final total monomer charge of approximately 40% by weight. Maintain at temperature for 48 hours. Terminate the reaction and purify the polymer as in Experimental 1.

EXAMPLES 1–8

The following examples represent nonaerosol hairspray compositions of the present invention.

The compositions are prepared as described above, by first mixing the polymer with the ethanol, neutralizing the polymer with sodium or potassium hydroxide, then adding sequentially (as applicable) with mixing, isododecane, plasticizer, perfume, and water. If sodium benzoate is used, it is added after water addition. Most preferably a premix of water and sodium benzoate is made and then added after the main water addition. Propellant for aerosol compositions are charged to conventional aerosol containers after the remainder of the prepared composition has been added.

While particular embodiments of the subject invention have been described, it will be obvious to those skilled in the art that various changes and modifications to the subject

| Component (wt %) | Example No. | | | | | | | |
|---|---|---|---|---|---|---|---|---|
| | 1 | 2 | 3 | 4 | 5 | 6 | 7 | 8 |
| Graft Polymer[1] | 4.00 | 5.00 | 6.00 | 5.50 | 6.00 | 6.50 | 5.00 | 4.00 |
| Isododecane[2] | 1.00 | 1.00 | — | 3.00 | 0.50 | 1.0 | 2.00 | — |
| Diisobutyl adipate | 0.40 | 0.75 | 0.90 | 0.55 | 1.52 | 1.30 | 0.75 | 0.40 |
| Sodium hydroxide[3] | 0.96 | 1.20 | 1.44 | 1.6 | — | 1.69 | — | 1.11 |
| Potassium hydroxide[4] | — | — | — | — | 1.35 | — | 0.44 | — |
| Perfume | 0.10 | 0.10 | 0.10 | 0.10 | 0.10 | 0.15 | 0.10 | 0.15 |
| Water | 17.00 | 20.00 | 20.00 | 18.00 | 11.05 | 20.00 | 13.71 | 39.24 |
| Sodium Benzoate | — | — | — | — | 0.10 | 0.10 | — | 0.10 |
| Ethanol[5] | 76.54 | 71.95 | 71.56 | 71.25 | 79.40 | 69.26 | 78.00 | 55.00 |

[1]Polymer of experimental 2, having a weight average molecular weight of about 150,000.
[2]PERMETHYL 99A, from Presperse, Inc., South Plainfield, NJ, USA.
[3]Sodium hydroxide is 30% active.
[4]Potassium hydroxide is 45% active.
[5]SDA 40 (100% ethanol).

EXAMPLES 9–14

The following examples represent aerosol hairspray compositions of the present invention.

invention can be made without departing from the spirit and scope of the invention. It is intended to cover, in the appended claims, all such modifications that are within the scope of the subject invention.

| Component (wt %) | Example No. | | | | | |
|---|---|---|---|---|---|---|
| | 9 | 10 | 11 | 12 | 13 | 14 |
| Graft Polymer[1] | 5.00 | 4.50 | 3.50 | 5.00 | 3.50 | 3.50 |
| Isododecane[2] | 0.50 | 0.50 | 2.00 | — | — | 0.50 |
| Triethyl citrate[3] | — | — | 0.21 | — | — | — |
| Diisobutyl adipate | 0.50 | 0.45 | — | 0.75 | 0.53 | 0.35 |
| Propylene glycol | — | — | 0.02 | — | — | — |
| Sodium hydroxide[4] | 1.11 | 0.94 | — | — | 0.78 | — |
| Potassium hydroxide[5] | — | — | 0.33 | 1.04 | — | 0.73 |
| Perfume | 0.10 | 0.10 | 0.10 | 0.10 | 0.10 | 0.10 |
| Water | 16.00 | 16.00 | 7.00 | 15.00 | 39.94 | 8.00 |
| Sodium Benzoate | 0.10 | 0.10 | — | 0.10 | 0.20 | — |
| Ethanol[6] | 56.69 | 57.42 | 62.85 | 53.99 | 30.00 | 54.5 |
| Propellant - Isobutane | — | — | 7.02 | 15.00 | 10.00 | — |
| Propellant - n-butane | 10.00 | 10.00 | — | — | — | — |
| Propellant - Dimethyl ether[7] | 10.00 | 10.00 | — | 15.00 | 15.00 | — |
| Propellant-Hydrofluorocarbon 152a[8] | — | — | 15.98 | — | — | 32.32 |

[1]Polymer of experimental 3, having a weight average molecular weight of about 150,000.
[2]PERMETHYL 99A, from Presperse, Inc., South Plainfield, NJ, USA.
[3]CITROFLEX-2, from Morflex, Inc., Greensboro, NC, USA.
[4]Sodium hydroxide is 30% active.
[5]Potassium hydroxide is 45% active.
[6]SDA 40 (100% ethanol).
[7]DYMEL-A, from Dupont.
[8]DYMEL-152a, from Dupont.

What is claimed is:

1. A hair styling composition comprising:
   (a) from about 0.1% to about 15%, by weight of the composition, of a graft adhesive copolymer, said polymer being characterized by a hydrophilic organic polymeric backbone having a hydrophobic macromonomer C covalently bonded and pendant from said backbone; wherein said polymeric backbone comprises hydrophilic A monomer units selected from the group consisting of unsaturated mono-, di- and poly- carboxylic acids, (meth)acrylamides, (meth)acrylates, (meth) acrylate alcohols, organic acid anhydrides, esters of organic acid anhydrides, hydrophilic vinyl compounds, hydrophilic allyl compounds, hydrophilic imides, salts of any such compounds, and mixtures thereof and wherein said polymer backbone has a $T_g$ of at least about −20° C.; said hydrophobic macromonomer C having a carbon based main chain, a $T_g$ of less than about 0° C. and a number average molecular weight of at least about 500; and
   (b) from about 99.9% to about 85%, by weight of the composition, of a carrier for said copolymer, said carrier comprising a hydrophilic solvent containing at least 0.5% ethanol, wherein said graft copolymer is substantially soluble in said hydrophilic solvent.

2. A hair styling composition as in claim 1, wherein said organic polymeric backbone comprises from about 10% to about 100%, by weight, of hydrophilic A monomer units selected from the group consisting of unsaturated mono-, di- and poly- carboxylic acids, (meth)acrylamides, (meth) acrylates, (meth)acrylate alcohols, organic acid anhydrides, esters of organic acid anhydrides, hydrophilic vinyl compounds, hydrophilic allyl compounds, hydrophilic imides, salts of any such compounds, and mixtures thereof and wherein and from about 0% to about 90%, by weight, of hydrophobic B monomer units selected from the group consisting of hydrophobic monomers selected from the group consisting of acrylic acid esters, methacrylic acid esters, N-alkyl acrylamides, vinyl compounds, vinylidene compounds, unsaturated hydrocarbons, and combinations thereof.

3. A hair styling composition as in claim 2, wherein said organic polymeric backbone comprises from about 15% to about 40%, by weight, of hydrophilic A monomer units and from about 60% to about 85%, by weight, of hydrophobic B monomer units.

4. A hair styling composition as in claim 2, wherein said hydrophilic A monomer units are selected from the group consisting of acrylic acid, methacrylic acid, N,N-dimethylacrylamide, dimethylaminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl pyrrolidone, vinyl ethers, maleimides, vinyl pyridine, vinyl imidazole, other polar vinyl heterocyclics, styrene sulfonate, allyl alcohol, vinyl alcohol, vinyl caprolactam, salts of any acids and amines listed above, and combinations thereof.

5. A hair styling composition as in claim 4, wherein said hydrophilic A monomer units are selected from the group consisting of acrylic acid, N,N-dimethyl acrylamide, dimethylaminoethyl methacrylate, quaternized dimethyl aminoethyl methacrylate, vinyl pyrrolidone, salts of the foregoing acids and amines, and combinations thereof.

6. A composition as in claim 2 wherein said hydrophobic B monomer units are selected from the group consisting of: acrylic or methacrylic acid ester of $C_1$–$C_{18}$ alcohols, dicyclopentenyl acrylate, 4-biphenyl acrylate, pentachlorophenyl acrylate, 3,5-dimethyladamantyl acrylate, 3,5-dimethyladamentyl methacrylate, 4-methoxycarbonylphenyl methacrylate, trimethylsilyl methacrylate, styrene, alpha-methylstyrene, t-butylstyrene, polystyrene macromer, vinyl acetate, vinyl neononanoate, vinyl pivalate, vinyl propionate, vinyl chloride, vinylidene chloride, vinyl toluene, isobutyl vinyl ether, s-butyl vinyl ether, butadiene, cyclohexadiene, bicycloheptadiene, 2,3-dicarboxylmethyl-1,6-hexadiene, ethylene, propylene, indene, norbornylene, β-pinene, α-pinene, and combinations thereof.

7. A compositions as in claim 6 wherein said hydrophobic B monomer units are selected from the group consisting of: n-butyl methacrylate, isobutyl methacrylate, t-butyl acrylate, t-butyl methacrylate, 2-ethylhexyl methacrylate, methyl methacrylate, and combinations thereof.

8. A hair styling composition as in claim 1 wherein said hydrophobic macromonomer C comprises a compound having the formula (I) or (II):

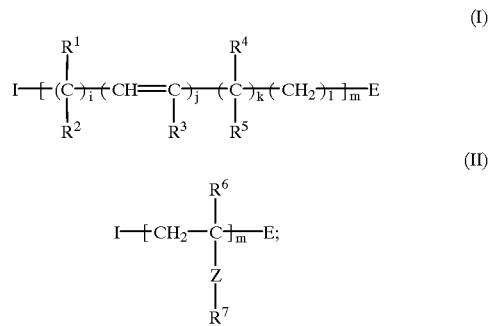

wherein
$R^1$, $R^2$, $R^3$, $R^4$ and $R^5$ are, independently, H or $C_1$ to $C_5$ straight or branched alkyl group;
$R^6$=H or $C_1$ to $C_8$ alkyl;
$R^7$=$C_4$ to $C_{18}$;

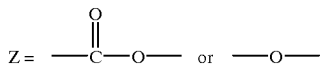

i and k are, independently, an integer of about 1 or greater;
j and l are, independently, an integer of about 0 or greater;
m is an integer of from about 10 to about 2000;
E is an ethylenically unsaturated endcapping group copolymerizable with said A monomer units, selected from the group consisting of acrylamide, methacrylamide, vinyl, allyl, acryloyl, methacryloyl, ethacryloyl, 2-vinylbenzyl, 3-vinylbenzyl, 4-vinylbenzyl, 2-vinylbenzoyl, 3-vinylbenzoyl, 4-vinylbenzoyl, 1-butenyl, 1-propenyl, isobutenyl, isoprenyl, cyclohexenyl, cyclopentenyl, and combinations thereof; and
I is a chemical initiator moiety.

9. The composition as in claim 8 wherein E is selected from the group consisting of vinyl, allyl, acryloyl, methacryloyl, ethacryloyl, 3-vinylbenzyl, 4-vinylbenzyl, 3-vinylbenzoyl, 4-vinylbenzoyl, 1-butenyl, 1-propenyl, isobutenyl, and combinations thereof.

10. The composition as in claim 9 wherein E is selected from the group consisting of vinyl, allyl, acryloyl, methacryloyl, ethacryloyl, 3-vinylbenzyl, 4-vinylbenzyl, and combinations thereof.

11. The composition as in claim 8 wherein said C macromonomer units are selected from the group consisting of acryloyl, methacryloyl, or 2-, 3- or 4-vinyl benzyl endcapped polymers of: methacrylic or acrylic acid esters, poly(alkenes), hydrogenated poly(alkenes), poly(vinyl ethers), poly(vinyl benzenes), and combinations thereof.

12. The composition as in claim 11 wherein said C macromonomer units are selected from the group consisting of acryloyl, methacryloyl, or 2-,3- or 4-vinyl benzyl endcapped polymers of: poly(n-butyl acrylate), poly(dodecyl acrylate), poly(2-ethylhexyl acrylate), poly(2-ethylbutyl acrylate), poly(n-ethyl acrylate), poly(n-heptyl acrylate), poly(n-hexyl acrylate), poly(iso-butyl acrylate), poly(iso-decyl acrylate), poly(iso-propyl acrylate), poly(3-methylbutyl acrylate), poly(2-methylpentyl acrylate), poly(nonyl acrylate), poly(octyl acrylate), poly(propyl acrylate), poly (2-ethylhexyl methacrylate), poly( tridecyl methacrylate), poly(hexyl methacrylate), poly(decyl methacrylate), poly(oct methacrylate), poly(octadecyl methacrylate), poly(dodecyl methacrylate), poly(n-pentyl methacrylate), poly(isobutylene), poly(isoprene), hydrogenated poly(1,2-butadiene), hydrogenated poly(1,4-butadiene), hydrogenated poly(isoprene), poly(1,2-butadiene), poly(1-butene), poly(5-methyl-1-hexene), poly (6-methyl-1-heptene), poly(4,4-dimethyl-1-pentene), poly (iso-butyl vinyl ether), poly[4-t-butyl vinyl benzene-co-2-ethylhexyl acrylate], poly[2-ethylhexyl acrylate-co-octyl acrylamide), poly[2-ethyl vinyl benzene-co-octyl methacrylate)], and combinations thereof.

13. A composition as in claim 1 wherein said graft copolymer is selected from the group consisting of: Poly [poly(acrylic acid/t-butyl acrylate)-graft-poly(isobutylene) macromonomer]; Poly[poly(dimethylaminopropyl methacrylate/t-butyl acrylate)-graft-poly(ethylhexyl methacrylate) macromonomer]; Poly[poly(acrylic acid/t-butyl acrylamide/t-butyl acrylate)-graft-poly(isobutylene) macromonomer]; and combinations thereof.

14. A composition as in claim 1, comprising from about 99.9% to about 20%, by weight of the composition, of said hydrophilic solvent.

15. A hair styling composition as in claim 1, further comprising an additional hydrophilic solvent selected from the group consisting of water, $C_3$ monohydric alcohols and mixtures thereof.

16. A hair styling composition as in claim 1, wherein said graft copolymer comprises from about 50% to about 99%, by weight of the composition, of said hydrophilic polymeric backbone and from about 50% to about 1%, by weight of the composition, of said hydrophobic macromonomer C.

17. A hair styling composition as in claim 16, wherein said graft copolymer comprises about 75% to about 95%, by weight of the composition, of said hydrophilic polymeric backbone and about 25% to about 5%, by weight of the composition, of said hydrophobic macromonomer C.

18. A hair styling composition as in claim 1, wherein said composition comprises no more than 80% of volatile organic compounds.

19. A hair styling composition as in claim 1, wherein said hydrophilic polymeric backbone has a $T_g$ of at least about 20° C. and said hydrophobic macromonomer C has a $T_g$ of less than about −25° C.

20. A hair styling composition as in claim 1, further comprising a volatile, saturated $C_{10}$–$C_{16}$ branched chain hydrocarbon.

21. A hair styling composition as in claim 20, wherein said hydrocarbon is isododecane.

22. A hair styling composition as in claim 1, further comprising a plasticizer.

23. A hair spray composition comprising a composition as in claim 1 disposed within a hair spray dispenser.

24. A hair styling composition consisting essentially of:
(a) from about 0.1% to about 15%, by weight of the composition, of a graft adhesive copolymer, said polymer being characterized by a hydrophilic organic polymeric backbone having a hydrophobic macromonomer C covalently bonded and pendant from said backbone; wherein said polymeric backbone comprises hydrophilic A monomer units selected from the group consisting of unsaturated mono-, di- and poly- carboxylic acids, (meth)acrylamides, (meth)acrylates, (meth) acrylate alcohols, organic acid anhydrides, esters of organic acid anhydrides, hydrophilic vinyl compounds, hydrophilic allyl compounds, hydrophilic imides, salts of any such compounds, and mixtures thereof and wherein said polymeric backbone has a $T_g$ of at least about −20° C.; said hydrophobic macromonomer C having a carbon based main chain, a $T_g$ of less than about 0° C. and a number average molecular weight of at least about 500;
(b) from about 99.89% to about 85%, by weight of the composition, of a carrier for said copolymer selected from the group consisting of water, $C_2$ to $C_3$ monohydric alkanols, and mixtures thereof;
(c) from about 0.01% to about 10%, by weight of the composition, of a plasticizer selected from the group consisting of glycerin, di-isobutyl adipate, butyl stearate, propylene glycol, $C_2$ to $C_8$ alkyl citrates;
(d) optionally, a non-surface active ionic strength modifier system, which when present, is present in an amount from about 0.1% to about 4%, by weight of the composition;
(e) optionally, a perfume, which when present, is present in an amount from about 0.05% to about 5%, by weight of the composition;
(f) optionally, a preservative, which when present, is present in an amount from about 0.05% to about 5%, by weight of the composition;
(g) optionally, a surfactant, which when present, is present in an amount from about 0.05% to about 5%, by weight of the composition;
(h) optionally, a hair conditioning agent, which when present, is present in an amount from about 0.05% to about 5%, by weight of the composition; and
(i) optionally, a propellant, which when present, is present in an amount from about 10% to about 60%, by weight of the composition.

* * * * *